United States Patent [19]

Hooven

[11] Patent Number: 4,744,786

[45] Date of Patent: May 17, 1988

[54] INFUSION PUMP

[75] Inventor: Michael D. Hooven, Miami, Fla.

[73] Assignee: Cordis Corporation, Miami, Fla.

[21] Appl. No.: 875,106

[22] Filed: Jun. 17, 1986

[51] Int. Cl.[4] .............................................. A61M 5/00
[52] U.S. Cl. .................................... 604/143; 604/246;
121/DIG. 12
[58] Field of Search ............... 604/143, 140, 141, 145,
604/246, 218, 211, 135, 134, 131, 151, 208, 207;
128/DIG. 12; 222/306.46

[56] References Cited

U.S. PATENT DOCUMENTS

| | | | |
|---|---|---|---|
| 2,017,276 | 10/1935 | Erickson | 604/143 |
| 2,168,437 | 8/1939 | Buercklin | 604/143 |
| 2,545,017 | 3/1951 | Billingsley | 604/143 |
| 3,474,787 | 10/1969 | Grant | 604/135 |
| 3,605,745 | 9/1971 | Hodosh | 604/143 |
| 4,561,856 | 12/1985 | Cochran | 604/211 |

Primary Examiner—Stephen C. Pellegrino
Attorney, Agent, or Firm—Henry W. Collins; Thomas R. Vigil

[57] ABSTRACT

The infusion pump delivers liquid to a body at an adjustably controlled rate of delivery. The pump comprises a syringe section including a syringe barrel having a nozzle at one end. A syringe piston has an inner end situated in the syringe barrel and an outer end extending out of the other end of the syringe barrel. A drive mechanism comprising a generally cylindrical housing has one end mounted to the other end of the syringe barrel. The outer end of the piston extends into the one end of the housing. A gas spring is situated at the other end of the housing and a dampening/timing mechanism is positioned between the gas spring and the outer end of the syringe piston. The dampening/timing mechanism includes a viscous fluid which is movable through a passageway in the housing from a space adjacent the gas spring to a space above the piston. A control mechanism is provided for altering the flow rate of the viscous fluid through the passageway and between the spaces.

20 Claims, 2 Drawing Sheets

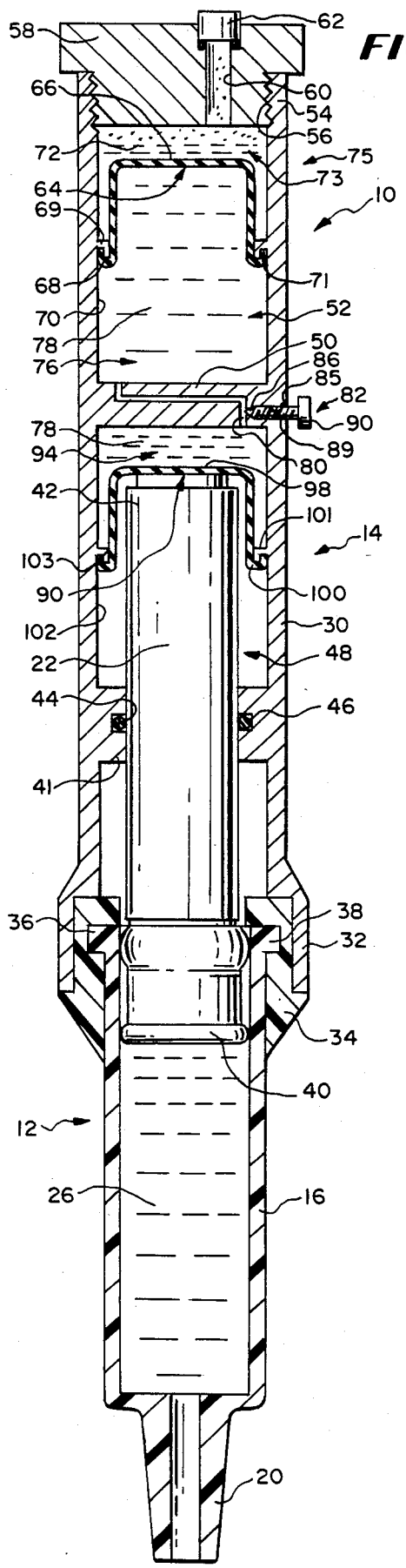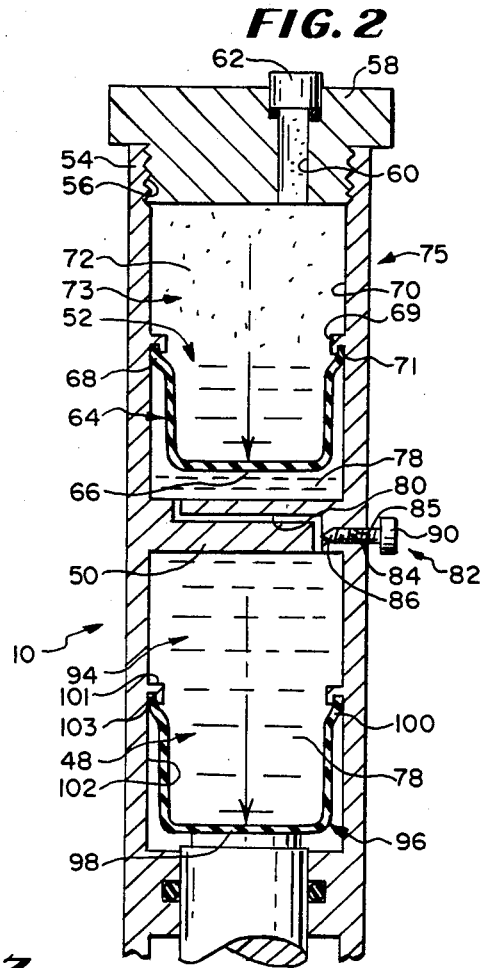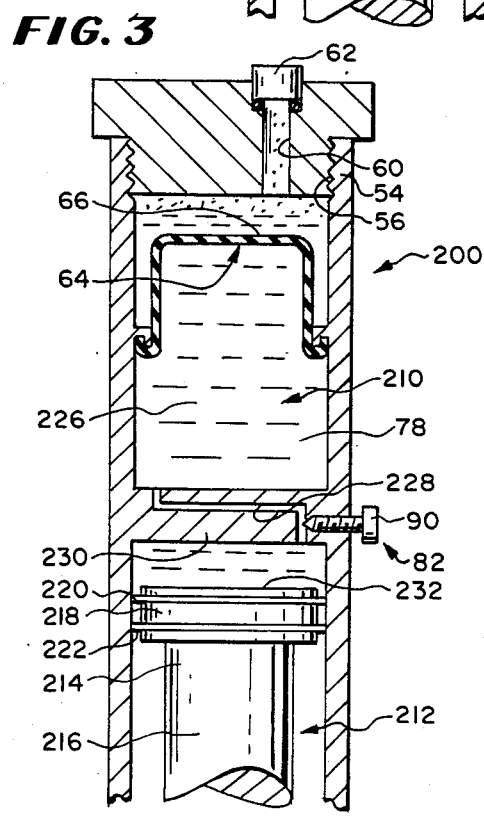

INFUSION PUMP

BACKGROUND OF THE INVENTION

1. Field of the Invention

The present invention relates to a syringe type pump having a drive mechanism therein for dispensing a liquid at a very slow controlled rate from a syringe barrel of the pump and a mechanism for adjusting the rate thereby to meter the dispensing of the liquid at a desired adjustable rate.

2. Description of the Prior Art

Heretofore various syringe devices and mechanisms associated therewith or incorporated therein for metering fluid from the syringe device have been proposed.

Examples of previously proposed syringe devices and other devices for dispensing liquid at a very slow metered rate are disclosed in the following U.S. patents:

| U.S. PAT. NO. | PATENTEE |
| --- | --- |
| 2,168,437 | Buercklin |
| 2,474,496 | Rayman |
| 2,545,017 | Billingsley |
| 2,605,765 | Kollsman |
| 2,706,480 | Nensel |
| 2,875,761 | Helmer et al. |
| 3,325,061 | Ellsworth |
| 3,433,223 | Black |
| 4,157,716 | Ruegg |
| 4,177,810 | Gourlandt |
| 4,190,048 | Sampson |
| 4,258,711 | Tucket et al. |
| 4,264,241 | Portner et al. |
| 4,274,558 | Clausen |
| 4,561,856 | Cochran |

Of these prior art patents, the Cochran U.S. Pat. No. 4,561,856 is the most pertinent and the infusion pump disclosed herein is an improvement over the infusion pump disclosed in the Cochran patent.

The Cochran patent discloses an infusion pump which has a drive mechanism in a housing of the pump. The drive mechanism includes a gas spring at one end of the housing which acts against a piston rod. The piston rod then extends through a timing capsule in the housing and has mounted thereon within the timing capsule a disc which has an outer diameter less than the diameter of the capsule. A viscous fluid is provided in the timing capsule and the other end of the piston rod bears against an outer end of a syringe piston, the inner end of which is received in a syringe barrel.

As the gas spring acts on the first end of the piston rod, it pushes the disc within the timing capsule against the viscous fluid which is caused to flow around the disc and through an annular space between the outer periphery of the disc and the inner diameter of the timing capsule to provide a fixed rate of, and non-adjustable throttling of, movement of the piston rod through the timing capsule which times or dampens the rate at which the piston rod exerts force on the outer end of the syringe piston.

As will be described in greater detail hereinafter, the infusion pump of the present invention, while also using a gas spring, differs from the previously proposed infusion pumps, and in particular the infusion disclosed in the Cochran U.S. Pat. No. 4,561,856, by providing a mechanism by which the gas spring acts directly against the viscous fluid which in turn acts against the outer end of the piston. The flow of the viscous fluid to a location at or adjacent the outer end of the syringe piston so as to transmit pressure thereagainst from the pressure of the gas spring is adjustably throttled, whereby the flow rate of the viscous fluid and thereby the rate at which force is applied against the outer end of the piston (and ultimately the rate at which liquid is dispensed from the syringe barrel) is adjustable. Further, this adjustable control of the flow rate of the viscous fluid, and the resulting dispensing of a liquid solution from the syringe barrel, is easily controllable from outside of the pump and is even adjustable during dispensing of a liquid solution from the syringe barrel.

SUMMARY OF THE INVENTION

According to the present invention there is provided an infusion pump for delivering liquid to a body at an adjustably controlled rate of delivery. The pump comprises a syringe section including a syringe barrel having a nozzle at one end. A syringe piston has an inner end situated in the syringe barrel and an outer end extending out of the other end of the syringe barrel. A drive mechanism comprising a generally cylindrical housing has one end mounted to the other end of the syringe barrel. The outer end of the piston extends into the one end of the housing. A gas spring is situated at the other end of the housing and a dampening/timing mechanism is positioned between the gas spring and the outer end of the syringe piston. The dampening/timing mechanism includes a viscous fluid which is movable through a passageway in the housing from a space adjacent the gas spring to a space above the piston. A control mechanism is provided for altering the flow rate of the viscous fluid through the passageway and between the spaces.

BRIEF DESCRIPTION OF THE DRAWINGS

FIG. 1 is a longitudinal sectional view through an infusion pump constructed according to the teachings of the present invention and shows the infusion pump in its primed or charged position.

FIG. 2 is a longitudinal sectional view of the drive mechanism of the infusion pump shown in FIG. 1 and shows the infusion pump in its exhausted or discharged position.

FIG. 3 is a fragmentary longitudinal sectional view of a modified embodiment of a drive mechanism of the infusion pump of the present invention.

DESCRIPTION OF THE PREFERRED EMBODIMENTS

Figure 4:
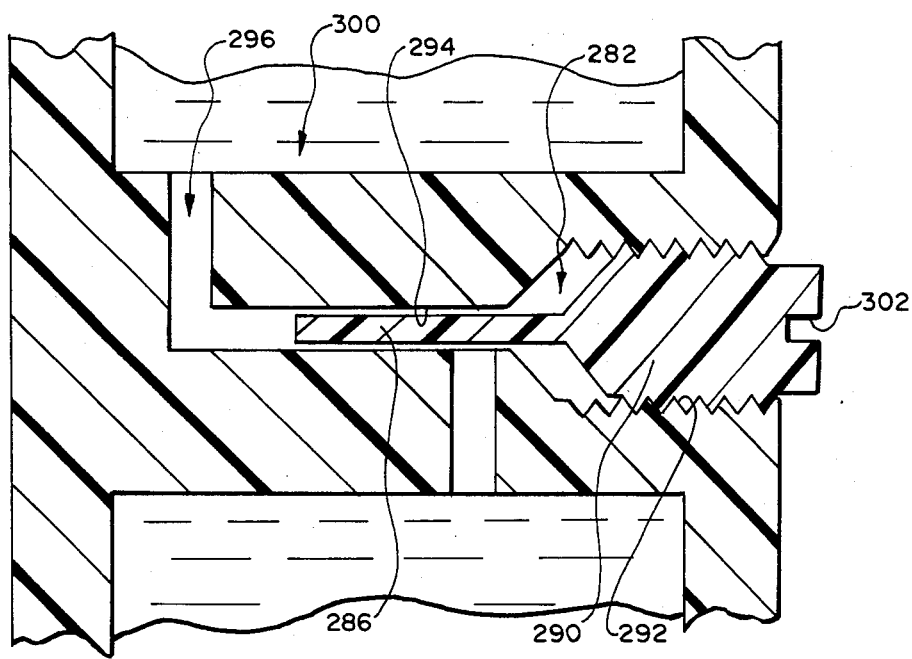
FIG. 4 is a fragmentary sectional view of one preferred embodiment of a needle valve of the infusion pump.

Referring now to FIG. 1 in greater detail, there is illustrated therein an infusion pump which is generally identified by reference numeral 10. The infusion pump 10 includes a lower syringe 12 and an upper drive mechanism 14.

The syringe 12 includes a syringe barrel 16 having a nozzle 20 at the lower end thereof and a syringe piston 22 received through the upper end 24 of the barrel 16. A liquid solution 26 having a predetermined concentration of a substance, such as insulin, a drug, or a nutrient therein, is drawn into the barrel 16 for being dispensed from the infusion pump 10 through the nozzle 20 in a manner described in greater detail below. For this purpose, the nozzle 20 is sized to receive a conventional catheter (not shown).

The other end of the catheter (not shown) can be connected to a needle (not shown) which is inserted into an individual's muscle, tissue or bloodstream for supplying the liquid solution 26 to the individual.

The drive mechanism 14 is coupled to the upper end 24 of the syringe barrel 16 and includes a generally cylindrical housing 30 which is shown as one piece but can be formed of several components.

Also, it is to be understood that at a lower end 32 of the cylindrical housing 30 there is mounted a bayonet type adapter 34 which is fixed to the lower end 32 of the housing 30 for receiving bayonet pins 36,38 at the upper end 24 of the syringe barrel 16, whereby the syringe barrel 16 and the pins 36,38 can be inserted longitudinally into and along the axis of the cylindrical housing 30 and then twisted to a releasably locked position as shown in FIG. 1.

As shown, the syringe piston 22 has a lower or inner end 40 received in the syringe barrel 16 and extends upwardly into the cylindrical housing 30 past an annular collar 41 to an upper or outer end 42. The annular collar 41 is shown integral with housing 30 but can be a separate piece press-fitted into the housing 30. The collar 41 has an annular slot 44 which receives and mounts an O-ring 46. The area above the annular collar 41 defines a first chamber and the upper end 42 of the syringe piston 22 is received in the first chamber 48. The O-ring 46 serves as a guide for the syringe piston, but does not act as a seal for chamber 48.

The upper end of the first chamber 48 is defined by an internal wall 50 which is shown formed integral with the cylindrical housing 30 but which can be formed separately and then fixed within the cylindrical housing 30 at the location shown.

The wall 50 separates the housing 30 into the first chamber 48 and a second chamber 52 which is located above the wall 50 and which is open at an upper end 54 of the housing 30 and has internal threads 56 at the upper end 54 thereof. A cap 58 is threadedly received in the upper end 54 of the cylindrical housing 30 to close off the second chamber 52. The cap 58 has a passageway 60 therethrough and a plug 62 for plugging the outer end of the passageway 60.

According to the teachings of the present invention, a movable mechanism is provided in each chamber 48 and 52. More specifically, there is provided in second chamber 52, a flexible rolling diaphragm 64, generally cylindrical in shape and having a closed end 66 and being open at the other end, the opening being defined by a rim or marginal area 68. The rim 68 is fixed to an annular flange 69 on an inner wall 70 of the second chamber 52 within an annular axially facing groove 71 in the flange 69 and approximately midway between the internal wall 50 and the cap 58. A fluid 72 (which can form a gas spring), such as Freon, is inserted through the passageway 60 into an upper portion 73 of the second chamber 52 above the diaphragm 64. Initially, most of the fluid 72 will be in the liquid phase with a small amount of the fluid 72 being in a gas phase. This gas phase will exert a constant pressure on the diaphragm 64 and, as the diaphragm 64 moves, more fluid in the liquid phase will go to the gas phase to maintain the pressure of the gas substantially constant. This phenomena, and a mechanism of this type, is referred to as a gas spring 74 and the space above the diaphragm 64 in the second chamber 52 is referred to as a drive section 75.

In a lower space 76 of the chamber 52 beneath the diaphragm 64 is a highly viscous fluid 78, such as a grease. The space 76 is referred to as a drive section 76.

As shown, a passageway 80, which can take various shapes and can have a diameter larger than the diameter shown, extends through the internal wall 50 and has a needle valve 82 associated therewith. The needle valve 82 includes a threaded needle 84 received in a threaded bore 85 in the wall 50 and has a needle point 86 movable into and out of the passageway 80 for throttling the flow through the passageway, and a knob 90 at an outer end of the threaded needle 84 which one can rotate to adjust the position of the valve 82. The needle valve 82 also can take various forms and one preferred embodiment of a needle valve (282 in FIG. 4) will be described below in connection with the description of FIG. 4.

As the gas pressure of the gas spring 74 forces the diaphragm 64 downwardly, viscous fluid 78, such as grease, is forced from the lower space 76 of the second chamber 52 through the passageway 80 (throttled by the needle valve 82) into an upper portion or space 94 of the first chamber 48.

In the first chamber 48 is situated another movable mechanism in the form of a second generally cylindrical flexible rolling diaphragm 96 having a closed end 98 and being open at the other end, the opening being defined by a rim or marginal area 100 of the diaphragm 96. The rim 100 is fixed to an annular flange 101 on inner wall 102 of the first chamber 48 within an axially facing, annular groove 103 in the flange 101 and approximately midway between the internal wall 50 and the annular collar 41. As shown, the rolling diaphragm 96 acts against the upper end 42 of the syringe piston 22.

In use, the knob 90 is turned until the needle valve 82 is in its fully open position. Then liquid solution 26 is forced through the nozzle 20 into the syringe barrel 16 against the lower end 40 of the syringe piston 22 to force the syringe piston 22 upwardly against the flexible rolling diaphgram 96.

This will cause the highly viscous fluid 78, such as grease, to be forced upwardly through the passageway 80 from the upper portion or space 94 of the first chamber 48 into the lower portion or space 76 of the second chamber 52 and against the diaphragm 66 to force most of the gas phase of the fluid 72 to go into its liquid phase.

At that point, the syringe piston 22 is in the position shown in FIG. 1 and the infusion pump 10 is now in its primed or charged position. Then, the pump 10 can be mounted to a catheter (not shown), such as an infusion catheter, for infusing liquid solution 26, such as an insulin solution, into a body at a predetermined basal rate.

The basal rate will be determined by the pressure of the gas phase in the gas spring 74, the position of the needle valve 82, i.e., the amount of constriction of the passageway 80, the viscosity of the highly viscous fluid 78 and the inner diameter of the syringe barrel 16. In any event, these parameters, particularly the throttling by the needle valve 82, can be controlled so as to provide a desired basal rate whereby the liquid being infused, such as insulin, will be infused at a desired adjustable steady or constant rate into the body, such as a human body. In this respect, the needle valve 882 is then set, i.e., rotated, to establish a desired rate of flow after the infusion pump 10 is in its primed or charged position shown in FIG. 1.

After a period of time, the rolling diaphragms 64 and 96 will be moved downwardly, as shown in FIGS. 1 and 2, from the primed or charged state of the infusion pump 10, shown in FIG. 1, to an exhausted or discharged state of the infusion pump 10, as shown in FIG. 2. At this point in time, the infusion pump 10, is disconnected from the catheter (not shown) to which it is attached and a new recharged or primed infusion pump 10 can be connected to the catheter in place of the exhausted or discharged infusion pump 10.

It will be noted that the viscous fluid 78, the passageway 80 and the needle valve 82 form an adjustable timing or dampening mechanism for timing or dampening movement of the syringe piston 22.

It is also important to note that another factor controlling the flow rate or basal rate of infusion, is the operating temperature. When the infusion pump 10 is used to infuse liquid into a human body, the infusion pump 10 is strapped to the human body so that the parameter of temperature, when the infusion pump is in use, is approximately the skin temperature of the human body, i.e. approximately 90° F.

In FIG. 3 there is illustrated a modified embodiment of an infusion pump 200 of the present invention. This modified infusion pump 200 has a second chamber 210 identical with the second chamber 52 of the infusion pump 10 shown in FIGS. 1 and 2.

However, in a first chamber 212, corresponding to the first chamber 48 shown in FIG. 1, the rolling diaphragm 96 is eliminated and instead, an upper end 214 of a syringe piston 216 has a larger diameter annular head 218 mounting two O-rings 220 and 222. Also, in this embodiment the annular collar 41 can be omitted if desired. However, such collar 41 can provide a stop for the head 218 if desired. In all other respects, the pump 200 is substantially identical to pump 10.

In this embodiment, a viscous fluid 226 or grease that passes through a passageway 228 in an internal wall 230 between the second upper chamber 210 and a first lower chamber 212 acts on an upper surface 232 of the head 218 and directly on the piston 216 rather than through a rolling diaphragm.

As shown in FIG. 4, one preferred embodiment of a needle valve is shown therein and is identified by reference numeral 282. The needle valve 282 includes a pin or needle portion 286 extending from a threaded head 290 which is received in a threaded bore 292. The pin portion 286 extends into a bore 294 forming part of a passageway 296 which includes the bore 294, that extends generally horizontal in FIG. 4, and an intersecting bore 298 across which pin portion 286 can extend. As shown, the pin portion 286 has a cross-section or diameter less than the cross-section or diameter of the bore 294. The more pin portion 286 is threaded into the bore 294, the slower the flow of a viscous fluid 300. Preferably, the head 290 has a slot 302 for receiving a screwdriver for enabling adjustment of the position of pin portion 286 in the bore 294.

From the foregoing description, it will be apparent that the infusion pump 10 or 200 of the present invention has a number of advantages some of which have been described above and others of which are inherent in the invention. In particular, it provides a simple mechanism for providing an adjustable desired basal rate of flow of a liquid to be infused into a body and a simple means, namely needle valve 82 or 282 for adjusting the basal rate or rate of infusion of the liquid solution 26, such as insulin solution, into a body. In this respect, the knob 90 or screw slot 302 provide for easy adjustment of the flow rate from outside the housing 30 and even during use, i.e., during a timed discharge or infusion of liquid solution.

Additionally, from the foregoing description, it will be apparent that modifications can be made to the infusion pump 10 or 200 of the present invention without departing from the teachings of the invention. Accordingly, the scope of the invention is only to be limited as necessitated by the accompanying claims.

I claim:

1. An infusion pump for delivering liquid to a body at an adjustably controlled rate of delivery, said pump comprising a syringe section including a syringe barrel having a nozzle at one end and an inner end of a syringe piston in said syringe barrel with an outer end of said syringe piston extending out of the other end of said barrel, a drive mechanism comprising a generally cylindrical housing having one end mounted to the other end of said syringe barrel, said outer end of said piston extending into said one end of said housing, a gas spring at the other end of said housing, dampening/timing means positioned between said gas spring and said outer end of said syringe piston, said dampening/timing means including a viscous fluid which is movable through a passageway in said housing from a space adjacent said gas spring to a space above said piston, and adjustment means for adjusting the flow rate of the viscous fluid through said passageway and between said spaces.

2. The infusion pump of claim 1 wherein said housing includes, a first chamber in said housing in which an outer end of said piston is received and a second chamber in said housing in which said gas spring is received, means separating said first chamber from said second chamber, said passageway and adjustment means being located in said separating means for allowing controlled flow of viscous fluid from said second chamber to said first chamber.

3. The infusion pump of claim 2 wherein said separating means comprises an internal wall within said housing between said first and second chambers.

4. The infusion pump of claim 3 wherein said adjustment means comprises throttling means for throttling the flow of fluid through said passage means in said internal wall.

5. The infusion pump of claim 4 wherein said throttling means comprises a needle valve and a threaded bore extending into said housing from the outside thereof and communicating with said passage means, said needle valve including a needle having a needle point movable into and out of said passageway, a threaded shank received in said threaded bore, and means for rotating said needle valve from a position exterior to said housing.

6. The infusion pump of claim 5 wherein said means for rotating said needle valve comprises a knob at the outer end of said needle.

7. The infusion pump of claim 4 wherein said passage means includes a first bore communicating with a transverse bore and said throttling means includes a needle valve including a pin portion which is received in and movable in said first bore and across said transverse bore.

8. The infusion pump of claim 7 wherein said dampening/timing means includes means for transmitting the pressure of said viscous fluid against said outer end of said piston.

9. The infusion pump of claim 8 wherein said pressure transmitting means comprises a flexible rolling diaphragm fixed to an inner wall of said first chamber and engaging said outer end of said piston.

10. The infusion pump of claim 9 wherein said flexible rolling diaphragm is generally cylindrical in shape and has a closed end arranged to act against said outer end of said piston and an upper open end defined by a rim which is fixed to said inner wall of said first chamber.

11. The infusion pump of claim 10 wherein said seal means comprise at least one O-ring.

12. The infusion pump of claim 8 wherein said pressure transmitting means includes a generally cylindrical head on the outer end of said piston and seal means between said head and said inner wall of said first chamber.

13. The infusion pump of claim 2 including first movable means between said viscous fluid in said first chamber and said piston and second movable means in said second chamber between said gas spring and said viscous fluid.

14. The infusion pump of claim 2 wherein said dampening/timing means includes a rolling flexible diaphragm in said second chamber and fixed to an inner wall of said second chamber to divide said second chamber into a drive section and a driven section, said drive section being defined between a closed end of said housing and said rolling flexible diaphragm and said driven section being defined between said rolling flexible diaphragm and said means for separating said housing into said first and second chambers, said gas spring being located in said drive section.

15. The infusion pump of claim 14 wherein said gas spring includes a fluid which is received in said drive section and which has a gas phase and a liquid phase with the gas phase exerting a constant pressure on said flexible rolling diaphragm.

16. The infusion pump of claim 2 wherein said housing has an inner annular collar therein positioned inwardly of the connection of said housing to said one end of said barrel and defining one end of said first chamber.

17. The infusion pump of claim 16 wherein said annular collar has an O-ring seal mounted therein for sealingly engaging said piston.

18. The infusion pump of claim 1 wherein said viscous fluid is a grease.

19. The infusion pump of claim 1 wherein said gas spring includes Freon gas.

20. A unitary infusion pump for controlling dispensing of a liquid from a syringe barrel, said pump comprising: housing means including a syringe barrel, a plunger situated in said syringe barrel and having an inner end and an outer end, drive means in said housing means positioned to cause relative movement between said syringe barrel and said plunger, said drive means including a sealed variable volume chamber, a viscous fluid in said chamber and motive means for causing relative movement between said syringe barrel and said plunger, by causing said viscous fluid to be displaced in said housing from said chamber, and means for throttling the displacement of said viscous fluid in said housing.

* * * * *